United States Patent [19]

Barfurth et al.

[11] Patent Number: 4,609,746

[45] Date of Patent: Sep. 2, 1986

[54] TITANIUM CHELATES AND PREPARATION OF THESE CHELATES

[75] Inventors: Dieter Barfurth, Troisdorf-Spich; Heinz Nestler, Troisdorf-Eschmar, both of Fed. Rep. of Germany

[73] Assignee: Dynamit Nobel AG, Cologne, Fed. Rep. of Germany

[21] Appl. No.: 658,489

[22] Filed: Oct. 9, 1984

[30] Foreign Application Priority Data

Oct. 12, 1983 [DE] Fed. Rep. of Germany ....... 3337098

[51] Int. Cl.$^4$ .............................................. C07F 7/28
[52] U.S. Cl. ..................................... 556/40; 106/300; 106/308 N; 502/171
[58] Field of Search ........................... 260/429.5, 429 J; 556/40

[56] References Cited

U.S. PATENT DOCUMENTS

| | | | |
|---|---|---|---|
| 2,824,114 | 2/1958 | Bostwick | 260/429.5 X |
| 2,935,522 | 5/1960 | Samour | 260/429.5 |
| 2,950,174 | 8/1960 | Legally | 260/429.5 X |
| 3,028,297 | 4/1962 | Legally | 260/429.5 X |
| 3,694,475 | 9/1972 | Brook et al. | 260/429.5 |
| 3,856,839 | 12/1974 | Smith et al. | 260/429.5 |
| 3,892,791 | 7/1975 | Brook et al. | 260/429.5 |
| 4,113,757 | 9/1978 | Kay | 260/429.5 |
| 4,159,209 | 6/1979 | Womersley | 260/429.5 X |
| 4,438,039 | 3/1984 | Beers et al. | 260/429.5 |

FOREIGN PATENT DOCUMENTS

| | | | |
|---|---|---|---|
| 2012924 | 9/1970 | Fed. Rep. of Germany | 260/429.5 |
| 2244462 | 5/1973 | Fed. Rep. of Germany | 260/429.5 |

*Primary Examiner*—Helen M. S. Sneed
*Attorney, Agent, or Firm*—Felfe & Lynch

[57] ABSTRACT

Organic titanium chelates which contain only acetylacetone and triethanolamine as ligands and chelating agents and are soluble in glycol ethers are disclosed. The addition of even a small amount of the glycol ether to these new substances improve the stability of their aqueous solutions in an extraordinary manner. Preferably, solutions of 50 to 80% of these new chelates are used, from which very dilute aqueous solutions, i.e., 1 to 5% of extraordinarily high stability can be made.

12 Claims, No Drawings

TITANIUM CHELATES AND PREPARATION OF THESE CHELATES

BACKGROUND OF THE INVENTION

The subject of the present invention is new titanium chelates containing acetylacetone and triethanolamine as chelating agents, as well as solutions of these chelates which are miscible with water.

Chelates of titanium with acetylacetone or triethanolamine are known as titanium acetylacetonate or triethanolamine titanates. In these chelates, two additional alkoxy groups are bound to the central titanium atom. They are generally in the form of solutions in the alcohols corresponding to the alkoxy groups, and are used as catalysts for crosslinking reactions, as coating material, or as adjuvants in the thixotropation of dispersions.

In the areas of application of these known compounds, there is an increasing need for using these reagents in small concentrations, principally in concentrations under 5% by weight, and for replacing the organic solvent largely with water. The obvious solution of this requirement, which is to dilute the above-named alcoholic solutions of these chelates with water, encounters the following difficulties.

If these alcoholic solutions are simply diluted with water, precipitates form. To prevent the occurrence of these precipitates, it has already been proposed, for the preparation of dilute titanium acetylacetonate solutions, to add acetic acid to the solutions prior to the addition of water, then add 13 times the amount of a 1:1 mixture of isopropanol and water, and then dilute them with water. Other proposals are, either first to add twice the amount of methyl ethyl ketone and then slowly stir the water in, or to stir the water in in the form of a mixture of 7 parts water and 3 parts isopropanol. These solvent dilutions, or even the concomitant use of methyl diglycol as solvent, do not, however, lead to a solution of the problem described, since in the course of time, precipitates again form from dilute aqueous solutions prepared in this manner, or they acquire turbidity, and this is undesirable in most applications of the titanium chelates.

The problem therefore was to make titanium chelate preparations available which can be diluted by the addition of water to titanium chelate contents of as little as 1% by weight, while the dilute aqueous solutions obtained are to be stable without the addition of further stabilizers, and are not to become turbid or tend to form precipitates, even after long periods of standing.

THE INVENTION

As a solution of this problem, new titanium chelates have been found which contain as ligands only the chelating agents triethanolamine and acetylacetone.

These new titanium chelates are highly viscous liquids having a titanium content between 15 and 17%, which are difficult to handle in pure form on account of their high viscosity. They are easily soluble in water, and these solutions, unless they are excessively diluted, have good keeping qualities. For example, 50% aqueous solutions of these new chelates display no turbidity or any settling out of precipitates, even after several weeks of standing. Only in the case of very great dilutions with water, at chelate contents of several percent, do precipitates settle out after several weeks of standing.

The new titanium chelates, however, are also very easily soluble in glycol ethers. Surprisingly, glycol ethers produce an extraordinary improvement of the stability of aqueous solutions of these new titanium chelates, so that mixtures of these titanium chelates with as little as 1%, by weight, of glycol ethers yield solutions, when diluted with water, which have an improved stability even in great dilutions with chelate contents between 1 and 5% by weight.

Solutions of the new titanium chelates in glycol ethers are those whose titanium chelate content is between 10 and 99%, and preferably between 50 and 80%, by weight. Such solutions are very stable, even after dilution with water to a chelate content of about 1% by weight; they have an outstanding compatibility with many resin systems, for example phthalat resins or polyacrylat resins, which, with the formerly known titanium compounds, immediately led to precipitation or turbidity. They are also compatible without any precipitation with ammonia, triethanolamine or 2-amino-2-methylpropanol, i.e., with compounds which serve as typical neutralizing agents in the manufacture of water varnishes.

The preparation of the new titanium chelates or their glycol ether solutions can be accomplished in different ways. One way is by the reaction of tetraalkoxytitanates with acetylacetone and triethanolamine in the stoichiometric ratio, followed by separation of the alcohol that is thus formed, preferably by distillation in the presence of glycol ethers. In this last case between the boiling points of the alcohol and of the glycol ether should be a difference of minimum about 30° C. The term, "stoichiometric ratio," used herein, is to be understood to refer to the amount of chelating agent that is necessary in order to split off all of the alkoxy groups of the titanium ester serving as starting material, in the form of the corresponding alcohol. The ratio of acetylacetone to triethanolamine can within the claimed scope be any desired ratio and differs between 1:1 and 2:067 with a total of 4 esterifiable OH-groups per titanium atom; preferably it amounts to 1:1.

In this type of preparation, the starting products can be the known titanium esters; for the better separation of the alcohol, short chain lengths of the ester component are more suitable than long ones. Examples of usable titanium esters are tetraethyltitanate, tetra-n-butyltitanate, tetraisobutyltitanate, tetra-n-propyltitanate, or tetraisopropyltitanate.

The new titanium chelate preparations, however, can also be produced by mixing dialkoxy-titanium-bis-acetylacetonates with dialkoxy-bis(triethanolamine)titanates and then separating the alcohol that has formed, preferred in the presence of glycol ethers. The separation of the alcohol is accomplished in this case the same as it was in the procedure described above.

Since in this procedure the titanium chelates used as starting products, whose alkoxy groups can be the same as in the case of the above-mentioned titanium esters, are generally in the form of solutions in those alcohols which correspond to the alkoxy group, the distilling of the alcohol must be continued until not only the originally bound alcohol but also the alcohol used as solvent has been removed as completely as possible.

In both of the indicated embodiments of the production of the new preparations, it is best to perform the distillation of the alcohol in the presence of as much glycol ether as is necessary to produce the solutions in the desired concentrations.

In the description of the present invention, the term "glycol ethers" is to be understood to mean both monoglycol ethers and polyglycol ethers. The corresponding general formula for them is HO—[A—O]$_n$—R, wherein A represents ethylen or propylen moieties, R represents alkyl moieties of 1 to 4 carbon atoms, and n can assume values between 1 and 8, preferably between 1 and 4. Examples of such glycol ethers are glycol monomethyl ether, glycol monoethyl ether, glycol monoisopropylether, glycol monobutyl ether, propylenglycol monomethyl ether, diglycol monomethyl ether, diglycol monoethyl ether, diglycol monobutyl ether and dipropylenglycol monomethyl ether.

An R'—C(O)O group, wherein R' represents an alkyl group of 1 to 3 carbon atoms, can take the place of the hydroxyl groups in the formula given above. Examples of such compounds, also known as glycol ether esters, are glycol monomethyl ether acetate or diglycol monobutyl ether acetate. Generally these glycol ether esters are also called alkyl glycol carboxylates; they react by transesterification to the same end products under corresponding conditions like the glycol ethers.

The titanium chelate preparations in accordance with the invention can be used in all applications in which the catalytic crosslinking or film forming action of titanates is desired; these new preparations are used successfully especially whenever the qualities of hydrolysis stability, good water solubility and good compatibility with substances or reactants are important.

EXAMPLES

Example 1

Preparation of a 50% solution of acetylacetone-triethanolamine-titanate (1:1:1) in methyl diglycol[2-(2-methoxy-ethoxy)ethanol], setting out from isopropyl titanate (a) In a one-liter flask with stirrer, thermometer, dropping funnel and reflux condenser, 284 g of isopropyl titanate (1 mole) is placed and, with stirring, 100 g of acetyl acetone (pentanedione-2,4, one mole) and then 149 g of triethanolamine (2,2',2"-nitrilotriethanol, one mole), are added in portions. The reaction mixture, which then warms up to about 70° C. is refluxed for 30 minutes by additional heat input to produce boiling.

(b) After cooling down to 50° C., 293 g of methyldiglycol[2-(2-methoxy-ethoxy)ethanol] is added, and the isopropyl alcohol that has developed from the solution in the reaction described in (a) is removed by distillation. The yield of isopropyl alcohol is 235.5 g (=98.1% of the theory). 590.5 g of a dark, reddish brown liquid is obtained, which has the following characteristics:

Index of refraction $n_D^{20}$ = 1.5160.
Density at 20° C. = 1.201 g/ml.
Viscosity at 20° C. = 168 mPa·s.
Flame point (DIN 51768) = 90° C.
Titanium oxid content = 13.5% (corresponding to 8.1% titanium content).

Solubility = clearly soluble in isopropanol, methyl ethyl ketone, toluene or methylene chloride. Such solutions are stable as 10% solutions, for example. Corresponding aqueous solutions also display this stability.

Example 2

Preparation of a 50% solution of acetylacetone-triethanolamine-titanate (1:1:1) in methyl diglycol, setting out from a mixture of titanium acetylacetonate and triethanolamine titanate (a) In a one-liter flask with stirrer, thermometer and reflux condenser, 242 g of commercial titanium acetylacetonate (a) 75% solution of diisopropoxy-bis-(2,4-pentanedionato)-titanate in isopropanol, approx. 0.5 mol) and 291 g of commercial triethanolamine titanate (80% solution of diisopropoxy-bis-(2,2',2"-nitrilotriethanolato)-titanium in isopropanol, approx. 0.5 mol) are mixed and refluxed with stirring for 30 minutes.

(b) After cooling to 50° C., 293 g of methyl diglycol (see Example 1) is added, and the isopropyl alcohol that was present as solvent and that has formed in the reaction under (a) is removed by distillation. The yield of isopropyl alcohol is 237.5 g (98.0% of the theory). 588.5 g of a dark, reddish brown liquid is obtained, which corresponds in its characteristics to the product of Example 1.

Example 3

Comparison of the solubility of the titanium chelate of the invention in water, in the range of concentration from 1 to 2.5%, to that of conventional titanium chelates

| | Solubility in desalted water at a titanium chelate concentration of | |
|---|---|---|
| Product | 1% | 2.5% |
| (a) Titanium chelate of the invention, Example 1 or 2 (50% sol. in methyl diglycol) | clear solution | clear solution |
| (b) Commercial titanium acetylacetonate, 75% solution in isopropanol | immediate formation of sediment | immediate formation of sediment |
| (c) Titanium acetylacetonate per (b), diluted with isopropanol to 50% | slightly turbid solution | slightly turbid solution |
| (d) Commercial triethanolaminotitanate, 80% solution in isopropanol | turbid solution | very turbid solution |
| (e) Triethanolaminotitanate per (d), diluted with isopropanol to 50% | turbid solution | very turbid solution |

Example 4

Use of the titanium chelate of the invention as a crosslinking additive for a water-diluted varnish on the basis of a phthalate resin LR 8525

Phthalopal LR 82525 ®, an acid phthalate resin (manufactured by BASF AG), is reacted by the following procedure to form a clear varnish:

250 g of this resin is dissolved in a mixture of 220 g of n-propanol, 500 g of water and 30 g of 25% ammonia solution. To this clear varnish was added, in each case, 1.5% of the titanium chelates listed in the table below. The clear varnishes thus modified had the following stabilities:

| Additive | Appearance of the clear varnish after 3 days of standing |
|---|---|
| Titanium chelate of the invention* | clear (even after 6 weeks of standing) |
| Commercial titanium acetyl acetonate of Example 3b | clear, slightly yellowish (point to pre-reaction) |
| Commercial triethanolamine titanate of Example 3d | turbid |

*(as a 50% solution in methyl diglycol)

The crosslinking action of the titanium chelate additives was tested with MEK after spreading the clear varnish on degreased aluminum and baking it on at 150° C. (45 minutes). The number of rubs with a cloth soaked in methyl ethyl ketone conducted by hand that are required in order to dissolve the varnish film away serves as a measure of the crosslinking of the varnish coating. The following was the result:

| | |
|---|---|
| Clear varnish with no additive | 1 rub |
| Clear varnish + titanium chelate of Example 1 | 64 rubs |
| Clear varnish + titanium acetylacetonate of Example 3b | 14 rubs |
| Clear varnish + triethanolaminotitanate of Example 3d | 71 rubs |

Example 5

Use of the titanium chelate of the invention as a crosslinking additive for a water-diluted binding agent on a polyacrylate basis The varnish solution which serves for testing compatibility and crosslinking action is prepared by diluting a commercial polyacrylate resin (BAYCRYL ®DA 50) with water in a 1:1 ratio. 2.5% of the titanium chelates listed below was added in each case to this varnish solution. The solutions thus modified had the following stabilities:

| Additive | Appearance of the clear varnish after 3 days of standing |
|---|---|
| Titanium chelate of the invention (50% solution) | clear, even after 6 weeks of standing |
| Commercial titanium acetyl acetonate of Example 3b | turbid immediately after addition |
| Commercial triethanolaminotitanate of Example 3d | turbid immediately after addition |

The crosslinking action of the titanium chelate of the invention is determined after baking a clear varnish coating on aluminum at 200° C. for 15 minutes. The resistance to methyl ethyl ketone (for description of the test see Example 4) increases from 1 rub in the case of plain clear varnish to 60 rubs in the case of the above-described mixture containing 2.5% of the titanium chelate of the invention.

Example 6

Preparation of an acetylacetone-triethanolamine-titanate (1:1:1) from isopropyl titanate In a one-liter flask with stirrer, thermometer, dropping funnel and reflux condenser, 284 g of isopropyl titanate (1 mole) is placed and, with stirring, 100 g of acetyl acetone (pentanedione-2,4, one mole) and then 149 g of triethanolamine (2,2',2"-nitrilotriethanol, one mole), are added in portions. The reaction mixture, which then warms up to about 70° C. is refluxed for 30 minutes by additional heat input to produce boiling.

After cooling down to 50° C. the reaction mixture is filled in a distilling apparatus, and the isopropyl alcohol that has developed in the above described reaction is removed by distillation in vacuo. The yield of isopropyl alcohol is 216.0 g (=90% of the theory). 317.0 g of a dark red liquid of high viscosity is obtained, which has the following characteristics:

Index of refraction $n_D^{50} = 1.563$.
Density at 50° C. = 1.238 g/ml.
Viscosity at 50° C. = 29,800 mPa·s.
Flame point (DIN 51768) = >75° C.
Titanium oxide content = 24.6%
Solubility = clearly soluble in isopropanol, methyl ethyl ketone, toluene or methylene chloride. Such solutions are stable as 10% solutions, for example. Corresponding aqueous solutions also display this stability.

Example 7

Preparation of an acetylacetone-triethanolamine-titanate (2:0.67:1) from titanium-acetylacetonate and triethanolamine In a one-liter flask with stirrer, thermometer and reflux condenser, 484 g of commercial titanium acetylacetonate (a 75% solution of diisopropoxy-bis-(2,4-pentanedionato)-titanate in isopropanol, approx. 1.0 mol) and 99.3 g of triethanolamine (2,2',2" nitrilotriethanol, 0.67 mole) are mixed. The reaction mixture is then warmed up and refluxed with stirring for 30 minutes.

After cooling down to 50° C. the reaction mixture is filled in a distilling apparatus, and the isopropyl alcohol that is present as solvent and that is developed in the reaction is removed by distillation in vacuo. The yield of isopropyl alcohol is 229.2 g (95.5% of the theory). 354.1 g of a dark red viscose liquid is obtained, which has the following characteristics:

Index of refraction $n_D^{50} = 1.568$.
Density at 50° C. = 1.227 g/ml.
Viscosity at 50° C. = 7100 mPa·s.
Flame point (DIN 51768) = >70° C.
Titanium oxide content = 22.2%
Solubility = clearly soluble in isopropanol, methyl ethyl ketone, toluene or methylene chloride. Such solutions are stable as 10% solutions, for example. Corresponding aqueous solutions also dispay this stability.

It will be understood that the specification and examples are illustrative but not limitative of the present invention and that other embodiments within the spirit and scope of the invention will suggest themselves to those skilled in the art.

We claim:

1. A chelate of tetravalent titanium, comprising only acetyl acetone and triethanolamine as ligands with a molar ratio of the two chelating agents of 1 to 2:1 to 0.67 and a total of 4 esterifiable OH-groups per titanium atom.

2. The chelate of claim 1, wherein the molar ratio of acetylacetone and triethanolamine is 1:1.

3. The chelate of claim 1 in solution in glycol ethers, wherein the chelate content is between 10 and 99%, by weight.

4. The chelate of claim 2 in solution in glycol ethers, wherein the chelate content is between 10 and 99%, by weight.

5. The chelate solution of claim 3 further comprising water as solvent in such an amount that the chelate content is between 1 and 5% by weight.

6. The chelate solution of claim 4 further comprising water as solvent in such an amount that the chelate content is between 1 and 5% by weight.

7. A method of preparing a titanium chelate solution comprising: reacting a tetraalkoxytitanate(IV) with acetylacetone and triethanolamine in a stoichiometric ratio between 1:1 and 2:0.67 to form a reaction product and heating the reaction product in the presence of glycol ethers until the alcohol formed in the reaction has largely been distilled out.

8. A method of preparing a titanium chelate solution comprising mixing dialkoxy-titanium-bis-(acetylacetonate) and dialkoxy-bis-(triethanolamino)-titanate to form a mixture and heating the mixture in the presence of glycol ether until the alcohol that has formed and any alcohol present as solvent are largely distilled out.

9. A product produced by reacting tetraalkoxy titanate(IV) with acetylcetone and triethanolamine.

10. A product produced by reacting dialkoxydiacetyl-acetotitanate and dialkoxy-bis-(triethanolamine)-titanate.

11. The chelate of claim 1 in solution in glycol ethers wherein the chelate content is between 50 and 80% by weight.

12. The chelate of claim 2 in solution in glycol ethers wherein the chelate content is between 50 and 80% by weight.

* * * * *